United States Patent
Novak et al.

(10) Patent No.: US 10,607,114 B2
(45) Date of Patent: Mar. 31, 2020

(54) TRAINED GENERATIVE NETWORK FOR LUNG SEGMENTATION IN MEDICAL IMAGING

(71) Applicant: Siemens Healthcare GmbH, Erlangen (DE)

(72) Inventors: Carol L. Novak, Newtown, PA (US); Benjamin L. Odry, West New York, NY (US); Atilla Peter Kiraly, San Jose, CA (US); Jiancong Wang, Philadelphia, PA (US)

(73) Assignee: Siemens Healthcare GmbH, Erlangen (DE)

( * ) Notice: Subject to any disclaimer, the term of this patent is extended or adjusted under 35 U.S.C. 154(b) by 129 days.

(21) Appl. No.: 15/872,304

(22) Filed: Jan. 16, 2018

(65) Prior Publication Data
US 2019/0220701 A1    Jul. 18, 2019

(51) Int. Cl.
| | | |
|---|---|---|
| *G06T 7/11* | (2017.01) |
| *G06K 9/62* | (2006.01) |
| *G06T 7/187* | (2017.01) |
| *G06T 11/00* | (2006.01) |
| *G06K 9/66* | (2006.01) |
| *G06T 5/00* | (2006.01) |
| *A61B 6/03* | (2006.01) |
| *A61B 6/00* | (2006.01) |
| *A61B 8/08* | (2006.01) |
| *G06T 7/10* | (2017.01) |

(52) U.S. Cl.
CPC ............ *G06K 9/6256* (2013.01); *A61B 6/032* (2013.01); *A61B 6/5211* (2013.01); *A61B 8/5207* (2013.01); *G06K 9/623* (2013.01); *G06K 9/66* (2013.01); *G06T 5/002* (2013.01); *G06T 7/10* (2017.01); *G06T 7/11* (2017.01); *G06T 7/187* (2017.01); *G06T 11/003* (2013.01); *G06T 2207/10081* (2013.01); *G06T 2207/20081* (2013.01); *G06T 2207/20084* (2013.01); *G06T 2207/20116* (2013.01); *G06T 2207/20152* (2013.01); *G06T 2207/30061* (2013.01); *G06T 2207/30101* (2013.01)

(58) Field of Classification Search
None
See application file for complete search history.

(56) References Cited

U.S. PATENT DOCUMENTS

| | | | | |
|---|---|---|---|---|
| 2007/0133894 A1* | 6/2007 | Kiraly | .................. | G06K 9/4609 382/260 |
| 2014/0298270 A1* | 10/2014 | Wiemker | ............... | A61B 6/466 715/849 |

OTHER PUBLICATIONS

Qi, S.—"Automatic pulmonary fissure detection and lobe segmentation in CT chest images"—BioMedical Engineering on Line 2014, pp. 1-9 (Year: 2014).*

(Continued)

*Primary Examiner* — Bernard Krasnic (57) ABSTRACT

A generative network is used for lung lobe segmentation or lung fissure localization, or for training a machine network for lobar segmentation or localization. For segmentation, deep learning is used to better deal with a sparse sampling of training data. To increase the amount of training data available, an image-to-image or generative network localizes fissures in at least some of the samples. The deep-learnt network, fissure localization, or other segmentation may benefit from generative localization of fissures.

17 Claims, 6 Drawing Sheets

(56) References Cited

OTHER PUBLICATIONS

Lassen, B.—"Automatic Segmentation of the Pulmonary Lobes From Chest CT Scans Based on Fissures, Vessels, and Bronchi"—IEEE 2013, pp. 210-222 (Year: 2013).*
Wei, Q.—"A Study on Using Texture Analysis Methods for Identifying Lobar Fissure Regions in Isotropic CT Images"—IEEE 2009, pp. 3537-3540 (Year: 2009).*
Badrinarayanan, Vijay, Alex Kendall, and Roberto Cipolla. "Segnet: A deep convolutional encoder-decoder architecture for image segmentation." arXiv preprint arXiv:1511.00561 (2015).
Chen, Chii-Jen, et al. "The Lobe Fissure Tracking by the Modified Ant Colony Optimization Framework in CT Images." Algorithms 7.4 (2014): 635-649.
Dai, Wei, et al. "Scan: Structure Correcting Adversarial Network for Chest X-rays Organ Segmentation." arXiv preprint arXiv:1703.08770 (2017).
Doel, Tom, David J. Gavaghan, and Vicente Grau. "Review of automatic pulmonary lobe segmentation methods from CT." Computerized Medical Imaging and Graphics 40 (2015): 13-29.
Kainz, Philipp, et al. "You should use regression to detect cells." International Conference on Medical Image Computing and Computer-Assisted Intervention. Springer, Cham, 2015.
Kiraly, Atilla P., et al. "Analysis of arterial sub-trees affected by pulmonary emboli." Georgia Institute of Technology, 2004.
Wei, Q., and Y. Hu. "A hybrid approach to segmentation of diseased lung lobes." IEEE journal of biomedical and healt informatics 18.5 (2014): 1696-1706.
Zhou, Shaohua Kevin, Jinghao Zhou, and Dorin Comaniciu. "A boosting regression approach to medical anatomy detection." Computer Vision and Pattern Recognition, 2007. CVPR'07. IEEE Conference on. IEEE, 2007.

* cited by examiner

TRAINED GENERATIVE NETWORK FOR LUNG SEGMENTATION IN MEDICAL IMAGING

BACKGROUND

The present embodiments relate to automated lung lobe segmentation. Knowledge of lobar boundaries is critical for radiologist reports and treatment planning. For example, if a patch of lung disease is found, knowing the lobar region helps with automated reporting and planning treatment or intervention. Knowing the completeness of a fissure separating lobar regions may also aid determining the future success of certain lobectomy procedures. Fissure regions may also be of assistance when performing a deformable registration across time points in volumes.

Fissures, which separate the lungs into lobar regions, appear as thin relatively hyperintense lines in computed tomography (CT) images. The fissure may vary in thickness and may be incomplete or missing in some patients. Accurate segmentation of the lungs into lobar regions is a difficult task for computers due to the wide variation of anatomies and imaging artifacts. Some common difficulties include: missing or incomplete fissures due to being too faint for the image resolution or truly missing from the particular patient, and image artifacts such as noise or patient motion. The typical absence of vessels near the fissures is commonly used to aid in automated lobe segmentation; however the existence of vessels crossing fissure boundaries is known to occur in some patients, presenting additional difficulties for automated methods.

Prior methods of automated lobar segmentation or fissure identification may have problems dealing with variance in fissure completeness and vessel crossings. A machine-learning approach based on the values of the Hessian matrix has been proposed for lobar segmentation, but there are difficulties in acquiring enough training data. Annotation of fissures on a CT volume is a difficult and tedious task. The experience and knowledge necessary to identify the fissures as well as their widely different appearance limits the number of users who can annotate the images. Even with machine learning, problems due to anatomic variation are not completely removed.

SUMMARY

By way of introduction, the preferred embodiments described below include methods, computer readable media, and systems for lung lobe segmentation or lung fissure localization, or for training a machine network for segmentation or localization. For segmentation, deep learning is used to better deal with a sparse sampling of training data. To increase the amount of training data available, an image-to-image or generative network localizes fissures in at least some of the samples. The deep-learnt network, fissure localization, or other segmentation may benefit from generative localization of fissures.

In a first aspect, a method is provided for lung lobe segmentation in a medical imaging system. A medical scanner scans the lungs of a patient, providing first imaging data representing the lungs of the patient. An image processor applies a machine-learnt generative network to the first imaging data. The machine-learnt generative network is trained to output second imaging data with labeled fissures as the response. The image processor segments the lobar regions of the lungs represented in the first imaging data based on the labeled fissures and the first imaging data. An image of the lobar regions of the lungs of the patient is output on a display.

In a second aspect, a system is provided for lung fissure localization. A medical scanner is configured to scan the lungs of a patient, where the scan results in image data representing the lungs of the patient. An image processor is configured to locate, with a machine-learnt image-to-image network, the fissures in the lung as represented in the image data. A display is configured to display an image as a function of the located fissures.

In a third aspect, a method is provided for machine training a network for lung lobe segmentation. Manual annotations of fissures in a first sub-set of slices of a volume representing the lungs are received. A fissure filter is applied to a second sub-set of slices of the volume. The fissure filters identify locations of the fissures in the slices of the second sub-set. A segmentation classifier is trained to segment the lobar regions based on the locations of the fissures in the slices of the second sub-set and the annotations of the fissures in the first sub-set. The trained segmentation classifier is stored.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A generative-trained fully convolutional network for fissure localization segments the fissure. The network may be trained with a discriminative network in an adversarial process. The network may be used to generate ground truth for deep learning a lung lobe segmentation classifier. The network may be used to localize the fissure for use in segmentation. The network may be used to indicate the location of the fissure for planning.

Current approaches to lobar segmentation have difficulty on the wide variety of lung images, requiring manual corrections on the results. Having fully or more reliable segmentation results makes lobar segmentation more practical and useful to physicians for diagnosis, prognosis, and/or planning. Although deep learning approaches are promising, direct application in an efficient way is not straightforward if detection of the fissure is desired. Using a generative model to localize the fissure allows for more effective deep learning. The generative network provides image-to-image region highlighting for the use of lobar segmentation of the lungs. The detection of the fissures themselves is also useful to assess their completeness, as this affects treatment planning.

The fissure localization may be used to create training data. The deep-learnt generative network for fissure highlighting may be used to avoid annotating all fissures to deep-learn a lobar segmentation classifier. A full deep-learning convolutional pipeline or architecture is provided for fissure localization and/or lobar segmentation. Part of the difficulty in creating a deep learning pipeline for segmentation is the availability of extensive annotated data on which to train.

Figure 1:
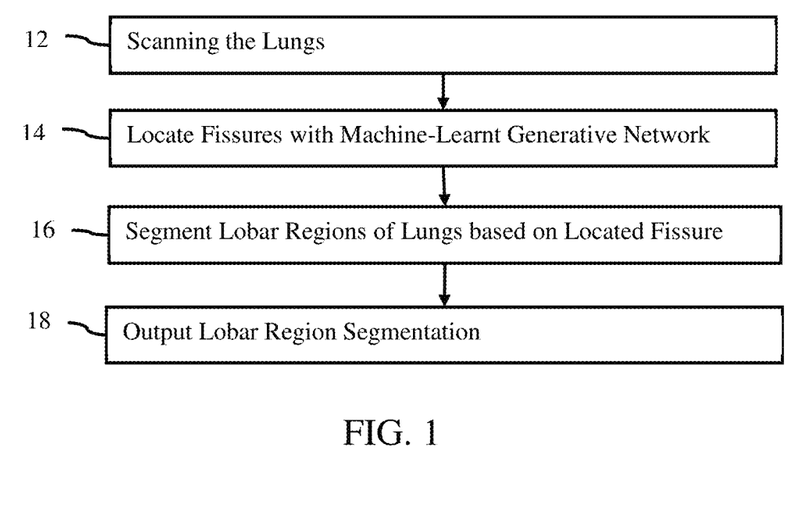
FIG. 1 is a flow chart diagram of one embodiment of a method for segmentation using localization of fissures by a machine-learnt generative network.

FIG. 1 shows a method for lung lobe segmentation in a medical imaging system. The segmentation uses a machine-learnt generative network to locate one or more fissures, which are then used for segmentation of one or more lobar regions of the lungs of a patient. The machine-learnt generative network may be used for other purposes, such as to provide training data for training a segmentation classifier.

The method of FIG. 1 is implemented in the order shown (e.g., top to bottom or numerical) or a different order. Additional, different, or fewer acts may be performed. For example, act 18 might be omitted. As another example, acts 12 and 14 might be performed without performing act 16. The fissure may be the end result, so act 18 could show an image of the fissure rather than of a lobar segmentation.

The method is implemented by a medical imaging system, such as any system for image processing from medical scans. The medical imaging system may be medical diagnostic imaging system, a review station, a workstation, a computer, a picture archiving and communication system (PACS) station, a server, a mobile device, combinations thereof, or another image processor. For example, the system shown in or described for FIG. 8 implements the method, but other systems may be used. A hardware processor of any type of system, interacting with memory (e.g., PACS database or cloud storage), display, and/or medical scanner, may perform the acts.

The acts may be performed automatically. The user causes the patient to be scanned or obtains scan data for the patient from a previous scan. The user may activate the process. Once activated, the fissures are located, the lobar regions are segmented, and a segmentation image is output to a display or medical record. User input of locations of the anatomy in any of the scan data may be avoided. Due to the generative network for fissure localization, there is less likely to be a need for user correction of the segmentation of the lobar region and/or fissure localization. Some user input may be provided, such as for changing modeling parameter values, correcting detected locations, and/or to confirm accuracy.

In act 12, a medical scanner scans the lungs of a patient. Herein, plural lungs and fissures are used, but a single lung and/or fissure may be used. The medical scanner generates imaging data representing a patient. The image or imaging data is made available by or within the medical scanner. Alternatively, the acquisition is from storage or memory, such as acquiring a previously created dataset from a PACS. A processor may extract the data from a picture archive communications system or a medical records database.

The imaging data or the medical image is a 3D volume of data representing the patient. The data may be in any format. While the terms image and imaging are used, the image or imaging data may be in a format prior to actual display of the image. For example, the medical imaging data may be a plurality of scalar values representing different locations in a Cartesian or polar coordinate format different than a display format. As another example, the medical image may be a plurality red, green, blue (e.g., RGB) values output to a display for generating the image in the display format. The medical image may be currently or previously displayed image in the display or another format. The imaging data is a dataset that may be used for imaging, such as scan data or a generated image representing the patient.

Any type of medical imaging data and corresponding medical scanner may be used. In one embodiment, the imaging data is a computed tomography (CT) image acquired with a CT system. For example, a chest CT dataset may be acquired by scanning the lungs. For CT, the raw data from the detector is reconstructed into a three-dimensional representation. As another example, magnetic resonance (MR) data representing a patient is acquired with an MR system. The data is acquired using an imaging sequence for scanning a patient. K-space data representing an interior region of a patient is acquired. Fourier analysis is performed to reconstruct the data from the k-space into a three-dimensional object or image space. The data may be ultrasound data. Beamformers and a transducer array scan a patient acoustically. The polar coordinate data is detected and beamformed into ultrasound data representing the patient.

The medical imaging data represents tissue and/or bone structure of the patient. For imaging the lungs, the imaging data may include response from the lungs and the anatomy around the lungs (e.g., upper torso). In other embodiments, the medical image represents both function (such as perfusion) as well as structure, such as nuclear medicine (NM) data.

The medical imaging data represents a two or three-dimensional region of the patient. For example, the medical imaging data represents an area or slice of the patient as pixel values. As another example, the medical imaging data represents a volume or three-dimensional distribution of voxels. The three-dimensional representation may be formatted as a stack or plurality of two-dimensional planes or slices. Values are provided for each of multiple locations distributed in two or three dimensions. The medical imaging data is acquired as one or more frames of data. The frame of data represents the scan region at a given time or period. The dataset may represent the area or volume over time, such as providing a 4D representation of the patient.

In act 14, an image processor applies a machine-learnt generative network to the imaging data. The machine-learnt generative model locates one or more fissures. In lung imaging, some fissures are "inferred" while others are clearly visible. The "inferred" fissures occur where the fissure is thin enough or the image noisy enough that the fissure is not visible in a displayed image. Inferred fissures also occur in cases where the patient has a complete of missing fissure. Tracing "inferred" fissures is useful for lobar segmentation but not for determining fissure completeness (i.e., whether the particular patient has a full fissure).

Since fissure localization from imaging data is the goal, the machine-learnt generative network is trained to detect "visible" fissures without filling in the "inferred" parts of the fissure. Although inferred parts may be localized by training the network in such a way, only visible fissures are localized in one embodiment for determining a complete lobar segmentation with further image processing.

The application of the generative network results in creation of a synthetic image. The synthetic image may be a spatial distribution of probabilities (i.e., probability map) representing the likelihood of being a fissure for each location. In other embodiments, the synthetic image may be the same imaging data but also include a label for the fissure. The generative network generates the label, such as with binarization from a soft max layer, or generates a probability map that is added to the input imaging data. Alternatively, the generative network generates imaging data that includes the fissure labels. The synthetic imaging data may have the label added to the scan data or image, such as having values that highlight the fissure with particular colors.

Figure 2:
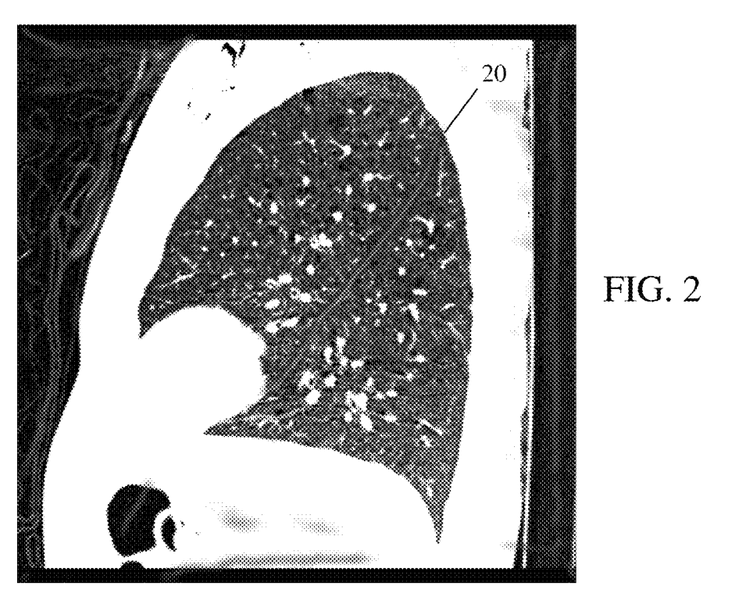
FIG. 2 is an example synthetic image with a localized fissure.

FIG. 2 is an example two-dimensional image generated by application of the generative network. The fissure 20 is highlighted, such as by intensity or color relative to surrounding tissue. The image shown is the input image overlaid with a binarization of a synthetically generated image by the generative network. For locations other than the fissure, the synthetic image data may be identical to the input imaging data from the scan.

Figure 3:
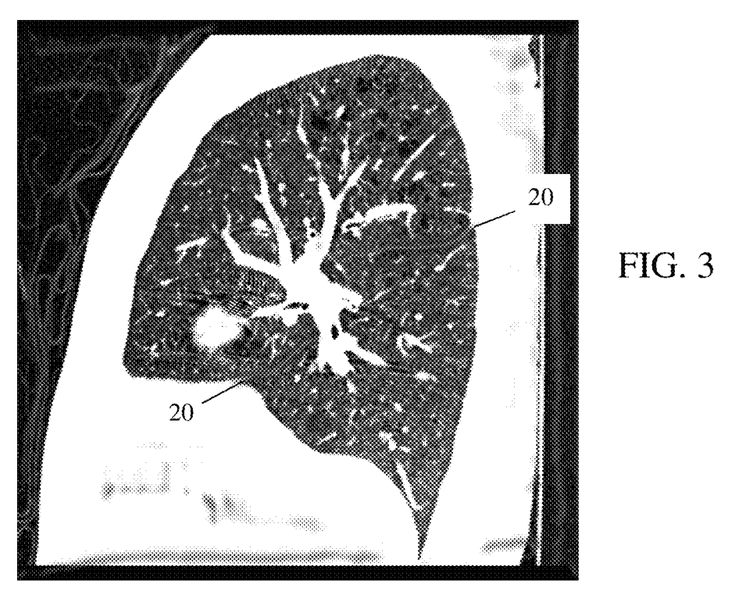
FIG. 3 is another example synthetic image with a localized, partial fissure.

In FIG. 2, the fissure 20 is complete. FIG. 3 shows an example synthetic image generated by the generative network with two partial fissures 20, which may be part of the same fissure but with a gap. The image includes an image from the input imaging data with an overlaid binary fissure label from the generative network for the fissures 20. The results show high sensitivity with a low false positive rate within the lungs. The responses outside of the lungs are not considered in determining sensitivity and false positive rate. Lung masking may be used so that the generative network localizes fissures only in the lungs. Since a synthetic image is generated, the fissure is localized in a non-binary way. A binary segmentation of the fissure is not used, so the synthetic image may be used for segmentation.

Any machine-learnt generative network may be used. The generative network is an image-to-image convolutional deep-learnt network. An image is input, and a synthetic image is output based on deep learnt convolutions and other operations. For application of the learnt generative network, the network only takes the imaging data as input, but other inputs may be provided, such as clinical data of a patient.

The generative network encodes the imaging data to a few independent latent variables, and generates synthetic data by sampling the latent variables. In deep learning, the latent variables are learned by machine training. The generative network returns a prior log-likelihood and is implemented as a piecewise-differentiable function, such as used in deep learning. For example, the generative network is a deep learnt model using restricted Boltzmann machines, deep belief network, neural autoregressive density estimators, variational auto-encoders, extensions thereof, or other deep learning approaches for generative modeling. In one embodiment, the trained deep generative network is a deep neural network with a set of j convolutional layers and k fully connected layers, each followed by a non-linear activation function, a set of pooling layers for features reduction, and a set of upscaling layers for image generation. Other layer arrangements may be used. The arrangement of SegNet, without a soft max layer to provide for a regression output, may be used.

Figure 4:
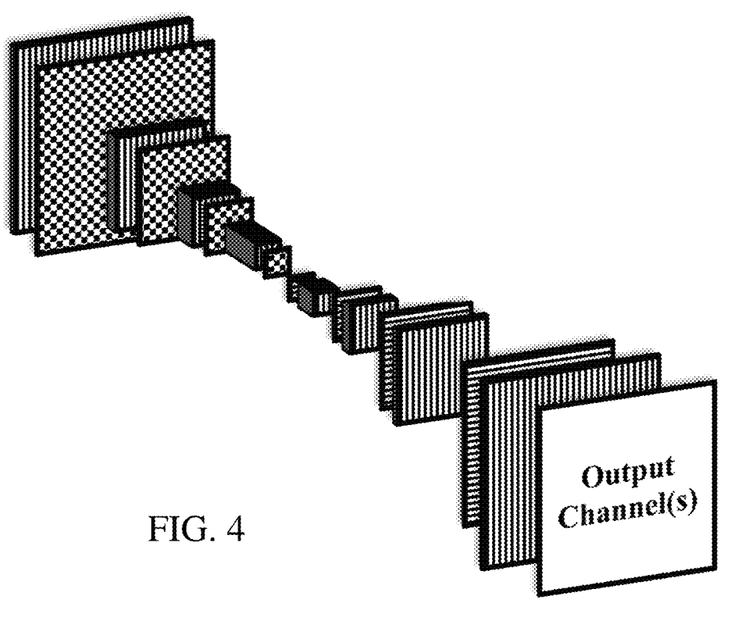
FIG. 4 illustrates an example image-to-image network architecture.

FIG. 4 shows one embodiment of a layer architecture for the generative network. Pooling layers are shown with a checker board pattern, convolution layers are shown with the vertical pattern, and upscaling layers are shown with a horizontal pattern. The thickness of the convolution layers or kernels represents the number of features. There are generally two parts in the architecture, one convolving learnt filters with increasing abstraction using pooling layers and a following part convolving learnt filters with decreasing abstraction using upscaling layers. Any amount of abstraction (feature reduction) and corresponding upscaling may be used. Any number of any type of layers in any arrangement with more or fewer portions may be used.

The input imaging data may be one of a 2D slice, 3D slab, 3D volume, or a 4D volume over time. Any number of output channels may be provided. Each output channel represents a synthetic image. Different channels may be provided for different fissures, for example. The number of features and/or output channels may be different. Additional features may lead to overfitting, so the number of features is set based on the number of training samples.

For training the generative network, a computer, workstation, server, or other processor accesses a database of hundreds or thousands of example images with known fissure locations. The machine learns the generative network from the images and ground truth fissure locations of the database. Using a piecewise-differentiable function or other deep learning function, the machine trains the deep generative network to output a spatial distribution of probability in response to an input image.

To train the generative model, the log-likelihood of the output is maximized. The generative model encodes features (i.e., kernels of the convolution layers) that represent the fissure location in the images. Since generative training is unsupervised, training does not require matched pairs of good and bad images, which is difficult to acquire on a large scale in a medical setting. To avoid localizing fissures outside the lungs, a pre-computed mask of the lungs is used during training to focus the training only within the regions of the lungs and ignore the outer regions.

The generative network is trained with deep machine learning to output probabilities by spatial location of the location in the input image including a fissure. The probability map is determined for any input imaging data. The probability map is a spatial distribution of probability of fissure or no fissure. The map is a spatial distribution, such as calculating the probability for each pixel or voxel based on the intensities or values of surrounding or neighboring pixels or voxels.

For training to output a probability map as the synthetic imaging data, the annotations of the fissures in the training data are blurred or probabilities assigned as a function of distance of a pixel or voxel from the actual fissure. For example, Gaussian smoothing is applied to the fissure mask or ground truth fissure locations. The image-to-image convolutional deep learning occurs using the resulting smoothed fissure masks as the ground truth. The network is not trained against a binarized mask, but against a probability of fissure appearance. This approach allows for a regression based approach for segmentation. By having a Gaussian mask for training, the output upon application is a probability map for the patient, not a binarized segmentation for the fissure. The probability map allows for further processing of the output, including binarization if desired.

The network parameters (e.g., machine trained features, kernels or layer values) are used to compute the probability for each pixel or voxel. Voxels or pixels with intensity and neighborhood intensity distribution that do not match those of the generative model will have a low probability, hence creating a map of potential fissure locations. Voxels or pixels with intensity and neighborhood intensity distribution that do match those of the generative model will have a high probability. Inverse probabilities may be used.

In one embodiment, the deep learning for the generative network uses a discriminator network. Generative adversarial training is used. The discriminator network is a neural network trained to determine whether a localized fissure is a ground truth (i.e., training data) or synthetically created by the generative network. The fissure as binarized, the fissure as a probability map, or the fissure with the imaging data is used for discrimination. The accuracy of fissure localization by the generative network may be increased using the adversarial training. Using a second network (i.e., discriminator network) to decide between a generated and ground truth fissure allows for an improvement in the results of the generative network being trained.

Figure 5:
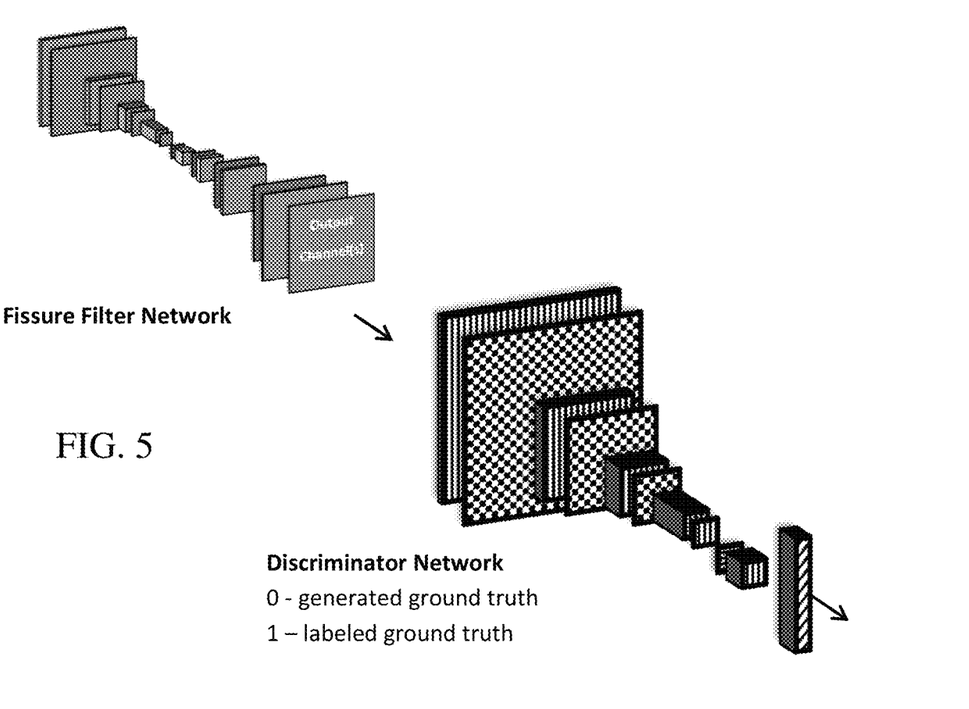
FIG. 5 illustrates another example image-to-image network architecture with a discriminator network used for training.

FIG. 5 shows an example. The generative network has a layer architecture as shown in FIG. 4. A discriminator network includes any layer architecture. In the example of FIG. 4, the discriminator network has a similar down sampling architecture portion of convolution layers and pooling layers as the generative network but reaches one or more fully connected layers (shown with diagonal lines) to discriminate between manually labeled and generated fissures. The fully connected layer may be a soft max layer for outputting a binary indication, such as a label as a generated or synthetic fissure or a ground truth fissure. One up sampling layer is shown, none or two or more up sampling layers may be provided.

Additional, different, and/or fewer layers or types of layers may be used for the generative network and/or the discriminator network. Skip connects (i.e., feeding features forward to non-adjacent layers), feedback, and/or max pooling indices may be used. A soft max final layer may be used to binarize the resultant fissure response.

The results from training the discriminator network are used to further train the fissure filter network. An iterative process is used, where both networks communicate results for training each other. The generative network uses the output of the discriminator network as an indication of sufficiency (i.e., the discriminator network ability to tell the difference from ground truth is to be minimized). The discriminator network uses the output of the generative network as an input to learn to discriminate.

Once trained, the generative network is applied without the discriminator network. The generative network outputs fissure localization in response to input of the imaging data. For example, a probability or binary mask indicating the fissure or fissures in the imaging data is output. In other embodiments, the generative network learns to output the lobar segmentation with or without also outputting the fissures.

One generative network may be trained to localize one or more fissures. The one network may be used to detect all fissures. One output channel may be used, such as one channel localizing (e.g., highlighting) all detectable fissures simultaneously. The generative network may be trained to include more than one output channel, such as a separate channel for each of the three fissures. In this case, the output channels are tailored to individually highlight different fissures. Multiple or different generative networks may be used, such as one network for each of left oblique, right oblique, and right horizontal fissures. In one embodiment, different generative networks are trained for the left and right lungs.

The generative model may localize in two dimensions (e.g., FIGS. 2 and 3) or in three dimensions. The fissures may be localized over time in 4D imaging data. In the example of FIG. 2, a 2D image is input and a single output marking all detected fissures is produced.

In one embodiment, the generative network of FIG. 4 is trained without the discriminator network of FIG. 5. Using Hessian input features for the machine learning, the generative network coupled with adversarial training has a 30% overall improvement in the fissure localization compared to the generative network alone. For the left oblique fissure, the error in fissure localization is reduced by 8%. For the right oblique fissure, the error in fissure localization is reduced by 50%. For the right horizontal fissure, the error in fissure localization is reduced by 35%. The fissure localization is derived from the probability map as a line fit that maximizes the probabilities while minimizing curvature or a region grown from a seed point of highest probability with a voxel accepted into the region based on a tolerance to the probability and the impact on an average local and/or global curvature of the region. Other approaches may be used. The error is an average distance from the detected fissure points to the nearest point on the ground truth fissure line.

In other embodiments, the generative network is trained to output the labeled fissure and the lobar boundaries. Both labels are generated by the generative network when applied. Simultaneous output of the outer lung segmentation may eliminate lung segmentation pre-processing usually required as a prelude to segmenting the lobar regions of the lungs. In yet other embodiments, the generative model is trained to output segmentation of one or more lobar regions.

Referring to FIG. 1, the image processor segments one or more lobar regions of the lungs in act 16. The segmentation locates one or more lobar regions of the lungs based on one or more fissures localized by the generative network. The imaging data and the fissure information, with or without additional input, is used to segment the lobar regions as represented in the imaging data. The resultant output of the fissure filter (i.e., generative network) is incorporated into a lobe segmentation algorithm by helping define the fissure boundaries. Since the generative network was trained only on visible fissures, incomplete and partial fissures are "inferred" or determined by the following segmentation algorithm. Fissures normally represent lobar region boundaries. Since parts of the fissure may not exist or may not be detectable in the scan data, the segmentation extends any incomplete or missing fissures by inferring their locations using other anatomical information, such as the locations of the airways and absence of large vessels. One output of the generative network may be a probability of the inferred part of the fissure (i.e., missing part). If lobes are annotated and fissure sections marked as visible or not, the generative network may output a confidence of the full path of the fissure.

Prior lobar segmentation methods may be used to define the surfaces of the lobar boundaries. For example, a minimum cost surface or thin plate splines may be used to compute the lobar region boundaries. The minimum cost based on distance to the fissure is used to locate the boundary of the lobe.

Figure 6:
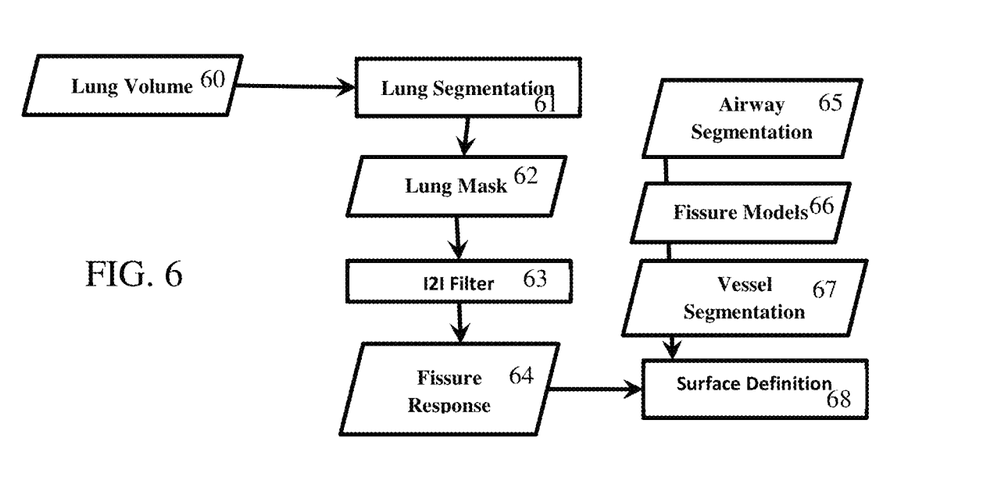
FIG. 6 is a flow chart diagram of an embodiment of a method for segmentation using the image-to-image network architecture of FIG. 4 or 5.

FIG. 6 shows one embodiment for segmentation of the lobes based on the fissure localization, airway locations, and vessel locations. The imaging data representing a lung volume 60 of a patient is input for lung segmentation in act 61. The resulting binary lung mask 62 is used to limit localization of fissures by the generative network in act 63 to the lungs. The fissure response 64, such as the probability map, binary fissure mask, or synthetic image data with fissure labeling, is used for defining the 3D surfaces that form the boundaries of the lobes in act 68. Other inputs are used for the surface definition of act 68. In terms of surface definition in act 68 for a minimum cost surface or spline, there are multiple approaches possible once the fissure regions are highlighted. As an example, the airway tree is segmented to identify general lobe regions in act 65, followed by segmentation of small vessels in the lungs in act 67 to identify regions that likely do not contain fissures based on fissure model 66, such as a statistical fissure model. Watershed or competitive region growing may be then be used to identify the lobes or 3D surface separating a lobe in act 68.

The generative network or image-to-image (I2I) filter detects 63 the visible fissure locations. The more accurate detection provides more useful information for defining the boundary of the lobe (i.e., for lobar segmentation). The input for the I2I filter 63 may operate on a 2D image (preferably sagittal slice), a 3D slab, or the entire volume if memory allows. The resultant fissure response 64 may be used to define the complete lobes using any segmentation, such as thin plate splines, competitive region growing, water shed transform, or other forms of surface definition. The segmentation extends any incomplete or missing fissure beyond the detected or localized portion of the fissure to fully define the lobar boundaries. This extension uses the response map or fissure response 64 in conjunction with the airway segmentation 65 and vessel segmentation 67. The segmentation may use a regression process based on the probability map.

Referring to FIG. 1, the image processor outputs an image to a display, such as LCD. Other outputs may be used, such as transfer over a network, storage in memory, or saving to a computerized medical record for the patient.

The output image is of the lobar segmentation of the lungs of the patient. The lobar regions are output as 2D images, for example by showing the original input data with the lobar boundaries overlaid in a different color; or by 3D images, for example by showing a surface rendering with each of the lobes in a different color. The lobar region may be extracted so that the image shows a representation of just one segmented lobar region, or just one of the lungs with their lobar regions. In alternative embodiments, the image shows the fissure as localized by the generative network without further segmentation of the lungs into lobar regions. In yet another embodiment, both fissure localization and lobar region segmentation are highlighted (e.g., by color or intensity), designated by a graphic (e.g., a boundary graphic), or otherwise indicated relative to other tissue.

The image includes an alphanumeric, graphical, or spatial representation of the lobar segmentation and/or fissure localization. The fissure or segmented region may be overlaid on an image of the anatomy of the lung. Any of the component maps, anatomy model, and/or spatial distribution from the generative model may be represented in the image.

The scan data may be used to generate an image of the lungs. The image may be a cross-section through the lungs. Alternatively, the image is a rendering of the three-dimensional distribution to a two-dimensional display, 3D holographic display, an augmented reality display, or virtual reality display. Any localized fissure or segmented lobe may be highlighted in the image.

Figure 7:
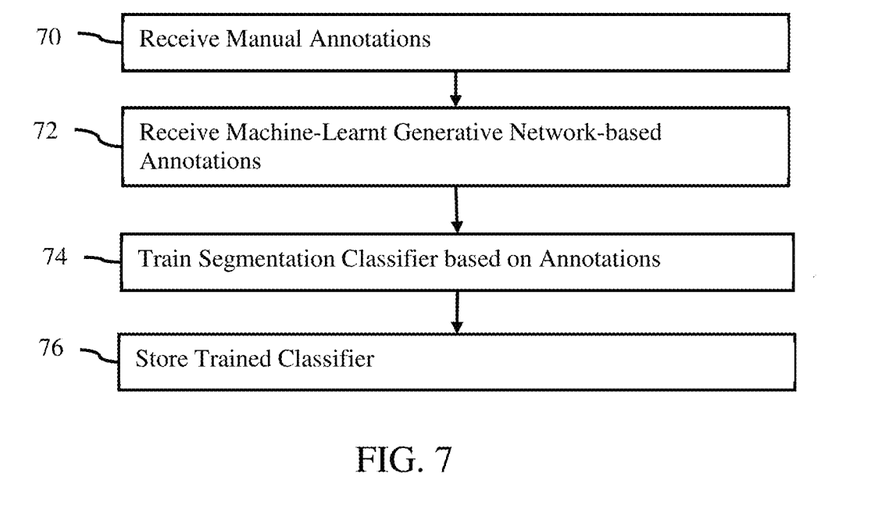
FIG. 7 is a flow chart diagram of one embodiment of a method for training a segmentation classifier.

FIG. 7 is a flow chart of one embodiment of a method for machine training a network for lung segmentation. Rather than manual programming of the lung segmentation to operate based on the fissure response, machine learning is used to create a machine-learnt classifier to segment the lobar region or regions. One input used in the training is from the previously trained generative network.

Figure 8:
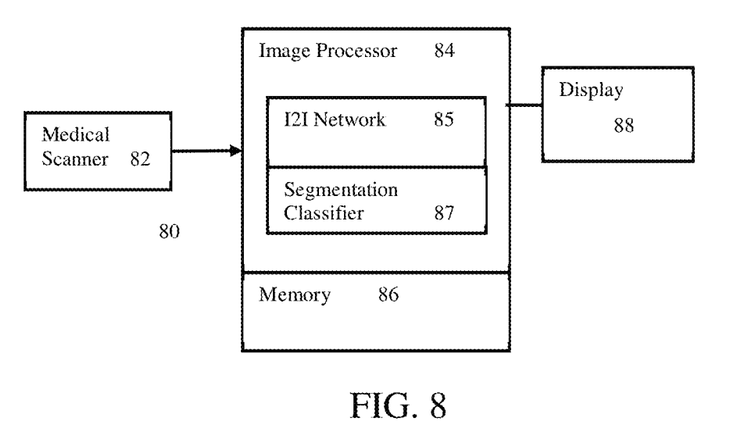
FIG. 8 is a block diagram of one embodiment of a system for fissure localization and/or lobar segmentation.

The method is implemented by the system of FIG. 8, a workstation, a server, a computer, or other image processor. While FIG. 7 is directed to training, the resulting machine-learnt classifier may be used by an image processor implementing act 16 of FIG. 1 or act 68 of FIG. 6.

The acts are performed in the order shown (top to bottom or numerical) or other orders. For example, acts 70 and 72 are performed in reverse order or simultaneously.

Additional, different, or fewer acts may be provided. For example, additional inputs (e.g., airway segmentation, vessel segmentation, and/or fissure model) may be provided for training.

Ground truth data is received for training. The ground truth data is received by loading from or accessing memory. Alternatively, the ground truth data is received over a computer network.

For training for segmentation, the ground truth data is segmentations based on imaging data. The training learns to relate an input feature vector to the ground truth segmentation. Where deep learning is used, the input feature vector is the imaging data with other information. For other types of machine learning, the input feature vector is information derived from the imaging data, such as Haar wavelets, steerable features, or values calculated from a Hessian matrix.

Other inputs in the feature vector for deep learning or other types of machine learning include fissure localization or lobar segmentation. The fissure information is used as an input to assist in determining the lobe boundary. Alternatively, the fissure information may be used as ground truth, such as to indicate locations of the boundary of a lobe for segmentation.

In act 70, the fissure annotations are received from an expert. Manual annotation may be used for some of the fissures. Alternatively, manual annotation is not used.

An expert user annotating a fissure may normally select both visible and inferred regions. "Inferred regions" refer to portions of the fissure that are not visible in a displayed image, but where someone with knowledge of lung anatomy judges that the lobar boundaries should be located based on other anatomical clues. Such annotations may be useful for defining a ground truth for a lobar region, but may be detrimental to developing a fissure highlighting method or segmentation designed to classify fissure completeness or presence. If the goal is to learn fissure completeness, manual annotation is only of the visible fissure. Alternatively, if the primary goal is lobar segmentation, the manual annotation includes the inferred locations of the fissure as well.

Another difficulty is the annotation itself. The fissures form a 3D surface through the volume and are difficult to annotate fully. Complete manual annotation of a single CT volume may take an individual 5 hours. Hundreds or thousands of volumes are desired for training.

To reduce this time, the manual annotation is performed sparsely. For example, the expert annotates every Nth sagittal or other slice in a volume. N is any integer greater than 1. In one embodiment, N=5 (the expert annotates every $5^{th}$ slice). Only a sub-set of the slices representing each volume are manually annotated, thereby allowing a single expert to annotate more patients in a given amount of time. The annotation may be sparse by full annotation of every Nth volume, so that some patient datasets receive no manual annotation.

In act 72, an image processor applies a fissure filter to the remaining samples (e.g., slices or volumes) that were not manually annotated. The fissure filter is a fissure segmentor or identifier, such as the image-to-image or generative network. The fissure filter outputs locations of the fissures.

The fissure filter automatically annotates the remaining samples for training. For example, the remaining slices of each volume or remaining volumes after manual annotation are annotated using the fissure filter. Extra samples may be provided by also annotating the manually annotated slices or volumes with the fissure filter. The locations of the fissures in imaging data not manually annotated are determined by the application of the fissure filter (i.e., generative network).

The expert may review the results from automatic annotation. This review may be more rapid than manual annotation without the automatic annotation. If any errors are found, the expert manually corrects the fissure location in the automatic annotation.

Based on using sparse manual annotation and automatic annotation for the remaining imaging data, a database with sufficient samples for machine learning is generated. The database may be more rapidly curated due to the use of the fissure filter.

In act 74, the image processor trains the segmentation classifier. The classifier is trained to segment a lobar region based on an input feature vector, such as imaging data, detected airways, detected vessels, and/or detected fissures. For example, the classifier is trained to segment one or more lobes of the lungs based on fissures in one or more slices. The training uses samples from the database, such as manually and automatically generated fissure locations, and ground truth for the lobar segmentation.

Any type of machine training and corresponding classifier may be trained. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used. Deep learning or deep reinforcement learning may be used to detect and segment the lobes. A neural network is trained using deep learning. Deep adversarial architectures may be used to improve the performance of the segmentation.

The classifier is trained from a training data set using a computer or other machine. Any number of annotated sets of data is used. For example, about 200 hundred volumes representing the lungs are annotated. The annotation indicates ground truth lobe boundaries within the volumes. This large number of annotations allows learning of relevant features of the input vector. The classifier learns various feature vectors for distinguishing between desired anatomical information and irrelevant information.

Where the training uses regression, the annotations of the fissures may be smoothed. For example, Gaussian smoothing of the fissures of the slices from the manual and/or automatically located fissures is performed. Where the generative network outputs a probabilistic map, smoothing is not needed. The manually annotated fissures are smoothed.

The machine (e.g., image processor) learns to identify locations of the lobe or lobes based on the input. In an iterative process, the training determines filter kernels, node values, weights, or other parameters of the classifier that relate the input feature vector to the desired output (i.e., ground truth).

In act 76, the learnt network or classifier is stored. The classifier is a matrix or architecture with learned values, kernels or another parameterization. The machine-learnt network is stored for application to an input feature vector for a given new patient.

The learnt network is stored in the memory with the training data or other memory. For example, copies of the learnt network are distributed to or on different medical scanners for use in hospitals or medical practices. As another example, copies are stored in a memory of one or more servers for segmentation as a service or remote segmentation.

FIG. 8 shows a system 80 for lung fissure localization. The system 80 implements the method of FIG. 1, FIG. 6, FIG. 7, or another method. The system 80 is for application of a machine-learnt generative network. Given input imaging data, the system 80 uses the generative network to generate a spatial distribution for localization of any fissures represented in the imaging data. The fissure localization may be further used to segment a lobar region of the lungs, to train a segmentation classifier, or output an image showing the fissure. While the system 80 is described below in the context of application of the previously learned generative network, the system 80 may be used to machine train the generative network.

The system 80 includes an image processor 84, a memory 86, a display 88, and a medical scanner 82. The image processor 84, memory 86, and display 88 are shown separate from the medical scanner 82, such as being part of a workstation, computer, or server. In alternative embodiments, the image processor 84, memory 86, and/or display 88 are part of the medical scanner 82. In yet other embodiments, the system 80 does not include the medical scanner 82. Additional, different, or fewer components may be used.

The medical scanner 82 is a CT, MR, ultrasound, camera, or other scanners for scanning a lung of a patient. In one embodiment, the medical scanner 82 is a CT system with an x-ray source and detector mounted to a moveable gantry for three-dimensional scanning of the upper torso of the patient. The image processor 84 or other processor of the medical scanner 82 performs computed tomography to determine scalar values for the tissue response to the x-rays in three dimensions.

The scan provides the scan data representing the lungs. The medical scanner 82 is configured by user settings or presets to scan the lungs of the patient, resulting in scan data representing all or at least part of the lungs of the patient. This imaging data is in any format, such as scalar values distributed in a regular or evenly dispersed 3D grid (i.e., uniform voxels).

The memory 86 is a buffer, cache, RAM, removable media, hard drive, magnetic, optical, database, or other now known or later developed memory. The memory 86 is a single device or group of two or more devices. The memory 86 is shown associated with or part of the image processor 84, but may be outside or remote from other components of the system 80. For example, the memory 86 is a PACS database storing the scan data from the medical scanner 82.

The memory 86 stores the scan data, machine-learnt generative network, machine-learnt classifier for lobar segmentation, and/or information used in image processing to localize the fissure and/or segment a lobe of the lungs. For example, the probability map output by the image-to-image network 85 is stored for use or access by the segmentation classifier 87. For training, the training data (i.e., input feature vectors including fissure localization and ground truth) are stored in the memory 86.

The memory 86 is additionally or alternatively a non-transitory computer readable storage medium with processing instructions. The memory 86 stores data representing instructions executable by the programmed image processor 84. The instructions for implementing the processes, methods and/or techniques discussed herein are provided on computer-readable storage media or memories, such as a cache, buffer, RAM, removable media, hard drive or other computer readable storage media. The machine-learnt generative network (I2I network 85) and/or segmentation classifier 87 may be stored as part of instructions for fissure localization and/or lobe segmentation. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 84 is a general processor, digital signal processor, three-dimensional data processor, graphics processing unit, application specific integrated circuit, field programmable gate array, digital circuit, analog circuit, quantum computers, combinations thereof, or other now known or later developed device for localizing a fissure and/or segmenting a lobe of the lung. The image processor 84 is a single device, a plurality of devices, or a network. For more than one device, parallel or sequential division of processing may be used. Different devices making up the image processor 84 may perform different functions, such as one processor localizing a fissure by application of the I2I network 85 and another processor segmenting a lobe by application of the segmentation classifier 87. In one embodiment, the image processor 84 is a control processor or other processor of a medical diagnostic imaging system (e.g., medical scanner 82). The image processor 84 is a hardware device configured by or operating pursuant to stored instructions, design (e.g., application specific integrated circuit), firmware, or hardware to perform various acts described herein.

The image processor 84 is configured to locate, with the machine-learnt I2I network 85, the fissures in the lungs as represented in the image data. The imaging data is input to the I2I network 85. By applying the I2I network 85 to the image data, the I2I network 85 generates a localization of one or more fissures represented in the imaging data. This generative network was trained to output a label for one or more fissures. The labeling has a spatial distribution at a same or different resolution as the input imaging data.

The image processor 84 may additionally be configured to segment the lobar regions of the lungs as represented in the image data based on the locations of the fissures. The output of the I2I network 85 is used in application of the segmentation classifier 87. Any algorithm for segmentation may be used. In one embodiment, the segmentation classifier is a machine-learnt network, such as a network trained with deep learning, to detect locations of one or more lobes based on input of imaging data with or without also input of localized fissures.

The image processor 84 may generate an image. The generative network output, segmentation classifier output, and/or imaging data are used to generate an image. The image is of the lungs of the patient with highlighting or relative indication of different parts, such as lobes and/or fissures. Any segmentation image or any image representing the localized fissures may be generated. The image provides added visualization of the lungs, fissures, and/or lobar regions of the lungs in addition to an image merely showing the detected tissue (i.e., highlighting or graphic for the localization and/or segmentation).

The display 88 is a CRT, LCD, plasma, projector, printer, or other output device for showing an image or other output of the image processor 84 and/or medical scanner 82. The display 88 displays an image of the lungs or part of the lungs. The localized fissures or lobe regions generated based on the localized fissures may be indicated or highlighted in the image for diagnostic or treatment use by a physician.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for lung lobe segmentation in a medical imaging system, the method comprising:

scanning, by a medical scanner, lungs of a patient, the scanning providing first imaging data representing the lungs of the patient;

applying, by an image processor, a machine-learnt generative network to the first imaging data, the machine-learnt generative network trained to output, in response to the applying, second imaging data as multiple different synthetic images from multiple different channels with one of the multiple channels and one of the multiple synthetic images being for one labeled fissure and another of the multiple channels and another one of the multiple synthetic images being for another labeled fissure, the multiple channels being part of an architecture of the machine-learnt generative network, wherein each output channel is separate and represents a synthetic image particular to one of the labeled fissures, the different synthetic images generated as single outputs by the machine-learnt generative network in response to input of the first imaging data;

segmenting, by the image processor, lobar regions of the lungs represented in the first imaging data based on the labeled fissures and the first imaging data; and outputting, on a display, an image of the lobar regions of the lung of the patient.

2. The method of claim 1 wherein scanning comprises scanning with the medical scanner being a computed tomography system.

3. The method of claim 1 wherein applying comprises applying the machine-learnt generative network as an image-to-image convolutional deep learnt network.

4. The method of claim 1 wherein applying comprises applying the machine-learnt generative network with a first portion of a layer architecture having first convolutional layers and pooling layers and a second portion of the layer architecture having second convolutional layers and upscaling layers.

5. The method of claim 4 wherein the first convolutional layers having an increasing number of features by layer through the first portion and the second convolutional layers having a decreasing number of features by layer through the second portion.

6. The method of claim 1 wherein applying comprises applying with the machine-learnt generative network having been trained with generative adversarial training.

7. The method of claim 6 wherein applying comprises applying with the machine-learnt generative network having been trained with the generative adversarial training using a discriminator network.

8. The method of claim 1 wherein applying comprises applying with the machine-learnt generative network trained to output the second imaging data with the labeled fissures indicating visible fissures of the lungs, and wherein segmenting comprises segmenting the lobar regions with boundaries including the visible fissures as well as inferred lobar boundaries that extend beyond the visible fissures.

9. The method of claim 1 wherein applying provides the labeled fissures as a probability map, the probability map being different than a binary segmentation, and wherein segmenting the lobar regions comprises segmenting with regression using the probability map.

10. The method of claim 1 wherein segmenting lobar regions comprises segmenting as a function of the labeled fissures, airway locations, and vessel locations.

11. The method of claim 1 wherein applying comprises applying with the machine-learnt generative network trained to output the labeled fissures and outer lung boundaries.

12. The method of claim 1 wherein outputting comprises outputting the lobar regions and an outer lung segmentation.

13. A system for lung fissure localization, the system comprising:
 a medical scanner configured to scan lungs of a patient, the scan resulting in image data representing the lungs of the patient;
 an image processor configured to locate, with a machine-learnt image-to-image network, fissures in the lungs as represented in the image data, the locations of the fissures represented in multiple different synthetic images output by the machine-learnt image-to-image network, the machine-learnt image-to-image network having multiple output channels, wherein one of the multiple output channels outputs the locations particular to one of the fissures represented in one of the multiple synthetic images and another of the multiple output channels outputs the locations particular to a different one of the fissures represented in another one of the multiple synthetic images, wherein each output channel is separate and represents a synthetic image particular to one of the fissures; and
 a display configured to display an image as a function of the located fissures.

14. The system of claim 13 wherein the medical scanner comprises a computed tomography scanner including the image processor.

15. The system of claim 13 wherein the image-to-image network comprises a generative network trained to output labels for the fissures.

16. The system of claim 13 wherein the image processor is further configured to segment lobar regions of the lungs as represented in the image data based on the locations of the fissures.

17. The system of claim 13 wherein the synthetic image is a non-binary spatial representation.

* * * * *